US010327698B2

(12) United States Patent
Biswas et al.

(10) Patent No.: US 10,327,698 B2
(45) Date of Patent: Jun. 25, 2019

(54) FOOD INTAKE MONITORING SYSTEM USING APNEA DETECTION IN BREATHING SIGNALS

(71) Applicant: Board of Trustees of Michigan State University, East Lansing, MI (US)

(72) Inventors: Subir Biswas, Okemos, MI (US); Bo Dong, Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 954 days.

(21) Appl. No.: 14/383,983

(22) PCT Filed: Feb. 28, 2013

(86) PCT No.: PCT/US2013/028179
§ 371 (c)(1),
(2) Date: Sep. 9, 2014

(87) PCT Pub. No.: WO2013/138071
PCT Pub. Date: Sep. 19, 2013

(65) Prior Publication Data
US 2015/0080672 A1 Mar. 19, 2015

Related U.S. Application Data

(60) Provisional application No. 61/611,265, filed on Mar. 15, 2012.

(51) Int. Cl.
*A61B 5/08* (2006.01)
*A61B 5/00* (2006.01)
(Continued)

(52) U.S. Cl.
CPC .......... *A61B 5/4866* (2013.01); *A61B 5/0826* (2013.01); *A61B 5/1135* (2013.01);
(Continued)

(58) Field of Classification Search
CPC ..... A61B 5/4866; A61B 5/725; A61B 5/6831; A61B 5/1135; A61B 5/0826;
(Continued)

(56) References Cited

U.S. PATENT DOCUMENTS

| | | | |
|---|---|---|---|
| 7,935,065 B2 | 5/2011 | Martin et al. | |
| 8,372,020 B2 | 2/2013 | Martin et al. | |

(Continued)

FOREIGN PATENT DOCUMENTS

| | | | | |
|---|---|---|---|---|
| FR | 2940038 A1 * | 6/2010 | .......... | A61B 5/1135 |
| FR | 2940038 A1 | 6/2010 | | |
| WO | WO-2006/116843 A1 | 11/2006 | | |

OTHER PUBLICATIONS

Support vector machine (Wikipedia), https://en.wikipedia.org/wiki/Support_vector_machine (pdf attached).*

(Continued)

*Primary Examiner* — Navin Natnithithadha
*Assistant Examiner* — Andrey Shostak
(74) *Attorney, Agent, or Firm* — Harness, Dickey & Pierce, PLC

(57) ABSTRACT

A wearable breathing sensor, such as a piezoelectric chest belt system, generates a breathing signal that is analyzed by a classifier to identify apnea patterns indicating that the subject has swallowed during breathing. These breathing signals are computer-analyzed to extract inferences regarding the subject's eating and drinking patterns and thereby provide useful data for monitoring food or beverage intake for remote health monitoring.

17 Claims, 17 Drawing Sheets

(51) Int. Cl.
*A61B 5/113* (2006.01)
*A61B 5/083* (2006.01)

(52) U.S. Cl.
CPC .......... *A61B 5/4205* (2013.01); *A61B 5/6831* (2013.01); *A61B 5/725* (2013.01); *A61B 5/083* (2013.01); *A61B 5/7246* (2013.01); *A61B 5/7264* (2013.01); *A61B 5/7282* (2013.01)

(58) Field of Classification Search
CPC ..... A61B 5/4205; A61B 5/083; A61B 5/7246; A61B 5/7282; A61B 5/7264
See application file for complete search history.

(56) References Cited

U.S. PATENT DOCUMENTS

2005/0283096 A1 12/2005 Chau et al.
2006/0064037 A1* 3/2006 Shalon ................ A61B 5/0006 600/586
2006/0282021 A1* 12/2006 DeVaul ................ A61B 5/0024 600/595
2007/0224126 A1* 9/2007 Dufresne ................ A61B 5/00 424/9.2
2010/0145166 A1* 6/2010 Pickler .................... A61B 5/16 600/301
2010/0160745 A1* 6/2010 Hills ........................ A61B 5/01 600/301
2011/0257505 A1* 10/2011 Suri ........................ A61B 6/504 600/408
2012/0209089 A1* 8/2012 Garde .................... A61B 5/103 600/301
2013/0255674 A1 10/2013 Martin et al.

OTHER PUBLICATIONS

English machine translation of the specification and claims of FR 2940038 A1 are attached.*
Alexandre Moreau-Gaudry et al: "Use of Respiratory Inductance Plethysmography for the Detection of Swallowing in the Elderly", Dysphagia, Springer-Verlag, NE, vol. 20, No. 4, Oct. 1, 2005 (Oct. 1, 2005), pp. 297-302, XP019366311, ISSN: 1432-0460 the whole document.

* cited by examiner

FOOD INTAKE MONITORING SYSTEM USING APNEA DETECTION IN BREATHING SIGNALS

CROSS-REFERENCE TO RELATED APPLICATIONS

This application is a National Stage of International Application No. PCT/US2013/028179 filed Feb. 28, 2013 and claims the benefit of U.S. Provisional Application No. 61/611,265 filed Mar. 15, 2012. The entire disclosures of each of the above applications are incorporated herein by reference.

GOVERNMENT RIGHTS

This invention was made with U.S. Government support under HL093395 awarded by the National Institutes of Health (NIH). The Government has certain rights in the invention.

FIELD

The present disclosure relates to food intake monitoring system and method. More particularly, the disclosure relates to a food intake monitoring system that uses sensors to detect apnea in the subject by monitoring breathing signals and that generates a stored record of the subject's eating patterns, useful in treating obesity, eating disorders and a variety of diseases that are linked to obesity.

BACKGROUND

This section provides background information related to the present disclosure which is not necessarily prior art.

According to the data from WORLD HEALTH ORGANIZATION, an agency of the United Nations, worldwide obesity has increased over 200% since 1980, and in US 68% of the population is considered to be overweight or obese (i.e. Body Mass Index greater than 25). It has been proven that obesity has causal relationship with a number of diseases such as coronary heart disease, type-2 diabetes, and various types of cancers (e.g. endometrial, breast and colon). With such findings, obesity control and management became an important medical, social, and policy issues in recent years. Two important components of obesity management are diet control and physical exercise.

Traditionally, researchers and health practitioners have used self-reported questionnaires for estimating both food intake and physical activity levels for high-risk individuals. In recent years, accelerometry-based instrumentation techniques are starting to emerge as alternatives to questionnaires for physical monitoring. For food intake monitoring, however, not many instrumented efforts were reported in the literature.

In most questionnaire based studies, participants have shown a tendency of intentionally or unintentionally under-reporting the amount of their food intake. Additionally, data self-reported by elderly people are often unreliable since amnesia is quite common among that population. It was also found that women are more likely to underreport their fat consumption while over-report their protein intake. It was experimentally shown that due to the above and other similar reasons, questionnaire based self-reporting systems are often too unreliable to be successfully used towards food intake monitoring for obesity management. An instrumented system, if available, could eliminate such subjectivity attached to questionnaire based systems.

Current solutions can be divided into two categories, invasive and non-invasive. Invasive methods, such as videofluoroscopy and functional magnetic resonance imaging (fMRI), cannot be used for everyday monitoring and dietary analysis. Many of the non-invasive methods use surface electromyography (SEMG) or movement sensors to measure the movement of larynx and the activity of the muscles associated with the swallow event. But these sensors are put at the neck, which would lead to the reluctance of the subjects to wear them. Some use Respiratory Inductance Plethysmography (RIP) to measure the movement of the chest, but these devices are quite expensive and are driven by other modules thus not suitable for wearable solutions.

SUMMARY

This section provides a general summary of the disclosure, and is not a comprehensive disclosure of its full scope or all of its features.

The present disclosure provides an instrumented system that can automatically monitor the duration of each instance of food/drink intake, which can in turn be used for estimating an individual's eating and drinking habits. Taking the self-reporting error out of the analysis, the system can have enormous significance in terms of the way today's obesity and disease management programs are implemented. For example, by analyzing data from a type-2 diabetes patient who also suffers from obesity, his or her health care provider may suggest the patient to eat less and do more exercise.

Disclosed here is a system and method that uses a wearable food and drink intake monitoring system that is capable of monitoring food and drink intake for remote health monitoring applications. In one embodiment a wearable sensor placed around the torso of the subject generates breathing signals that are processed by a classifier to identify apnea patterns indicating that the subject has swallowed. In another embodiment a template matching mechanism is deployed to more accurately perform swallow analytics. Post-processing algorithms, such as Consecutive Swallow Amalgamation and averaging reference cycles, are used in some embodiments to improve the accuracy and effectiveness of the system. Other embodiments further improve system accuracy by automatically analyzing patterns of sequence. The disclosed system and method can be deployed, if desired, in a food and drink intake real time monitoring system, which can be used for various purposes, such as health improvement, assisted living and disease monitoring.

The disclosed system thus provides a system and method for monitoring food or beverage intake of a living subject, utilizing a wearable breathing sensor adapted to be worn around the torso of the subject and being responsive of inhale-exhale movement of the subject's torso to produce a breathing signal expressed as electrical data. The electrical data are analyzed by a classifier receptive of the electrical data and operative to classify the electrical data according to a predefined set of breathing patterns that include at least one apnea pattern indicating that the subject has swallowed during a breathing cycle. If desired, a swallow pattern analyzer operates upon the output of the classifier to recognize food and beverage intake patterns associated with eating and drinking different types of food and beverage and optionally associate those patterns with other data, such as eating log data entered by the subject, geolocation data automatically captured, and time and date data corresponding to the detected intake patterns.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 4A:
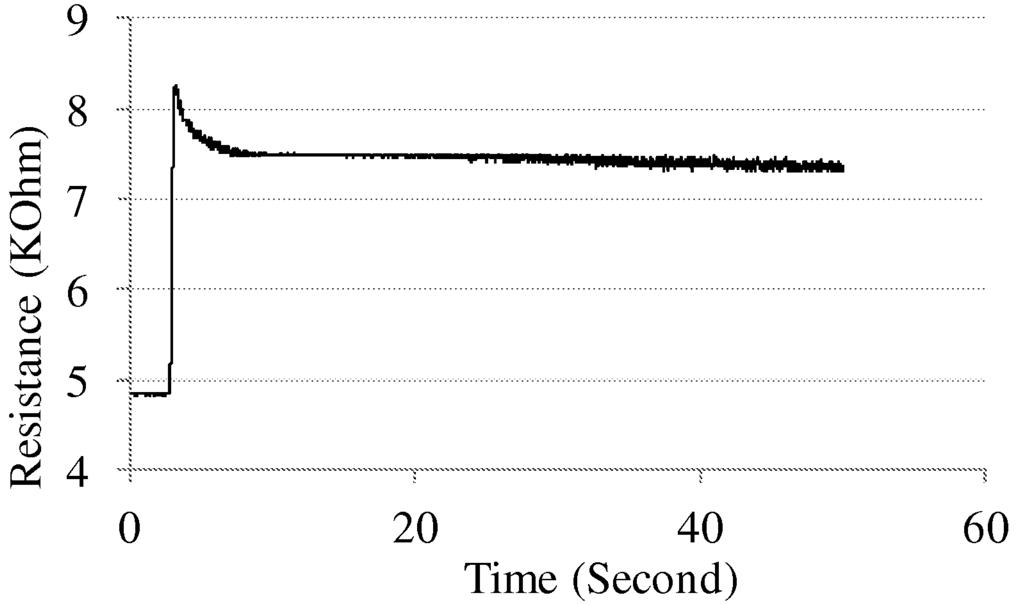
Figure 4B:
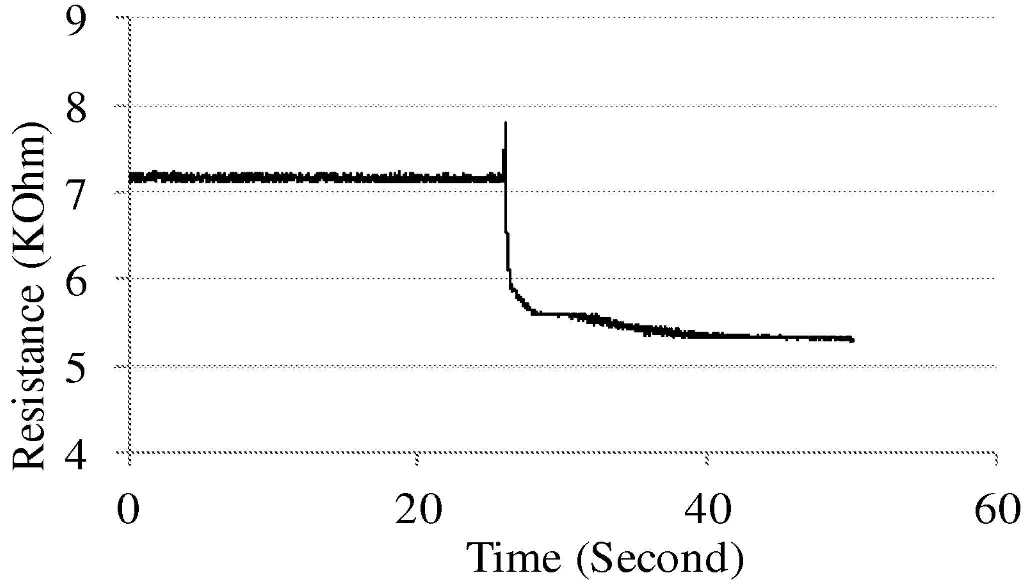
Figure 5:
Figure 6:
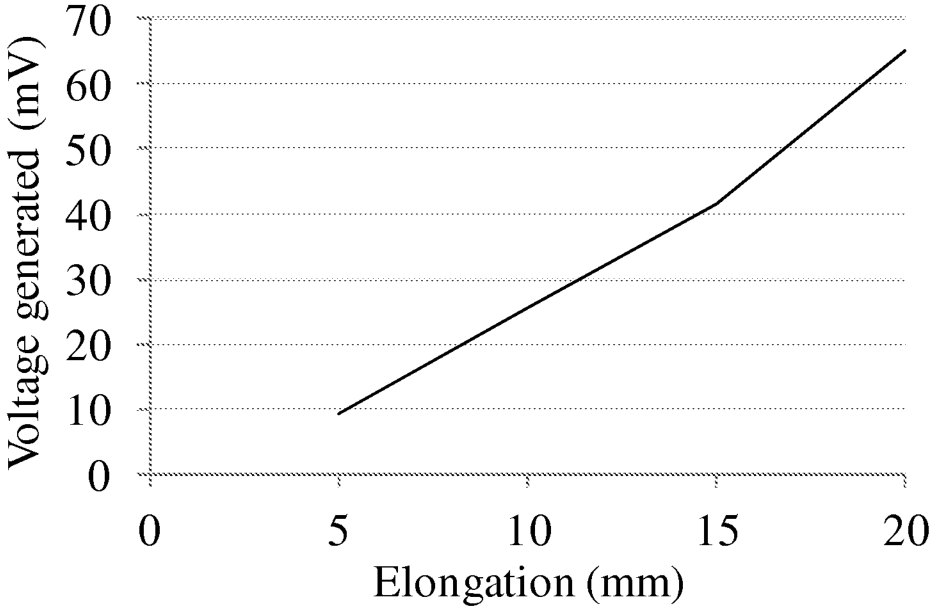
Figure 7:
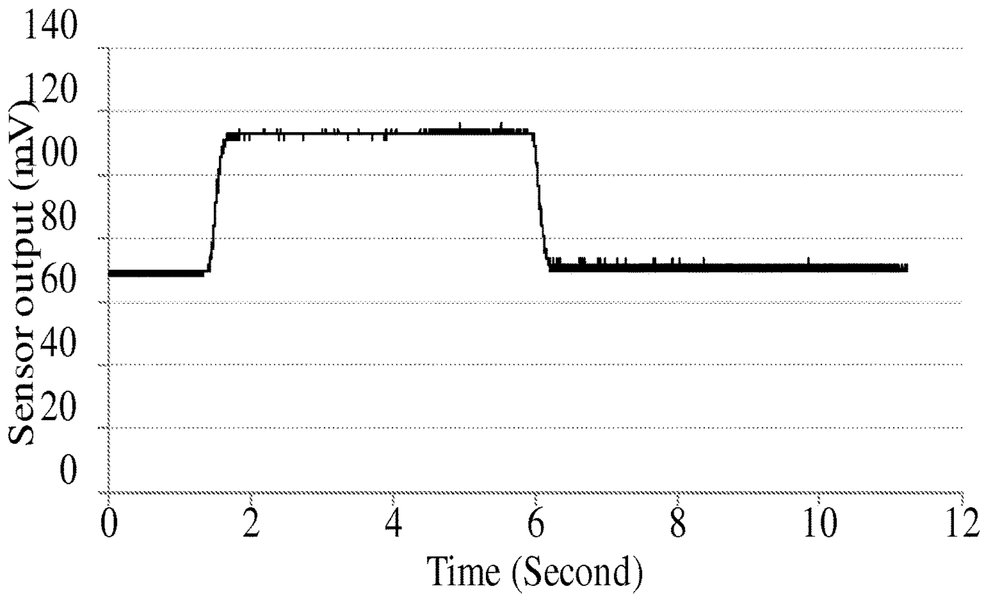
Figure 8:
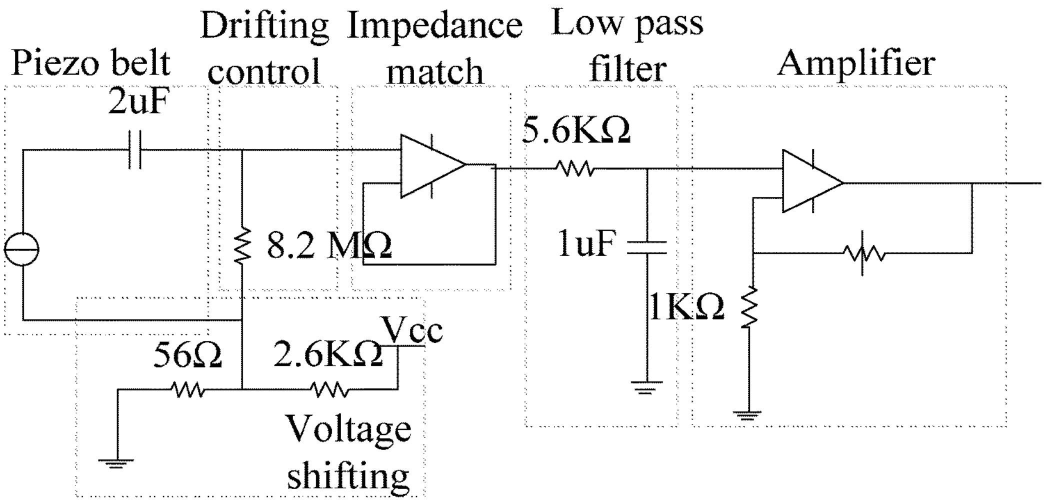
Figure 9A:
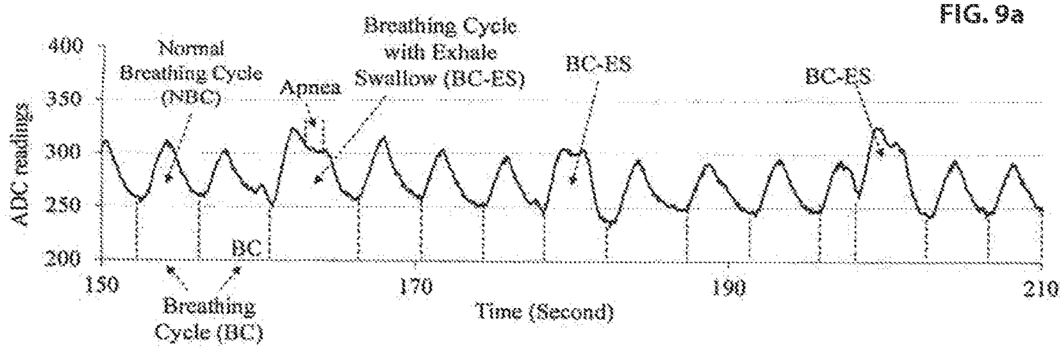
Figure 9B:
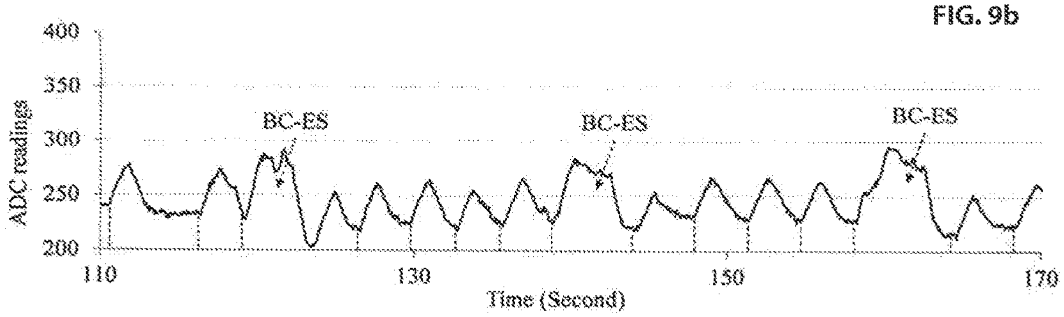
Figure 9C:
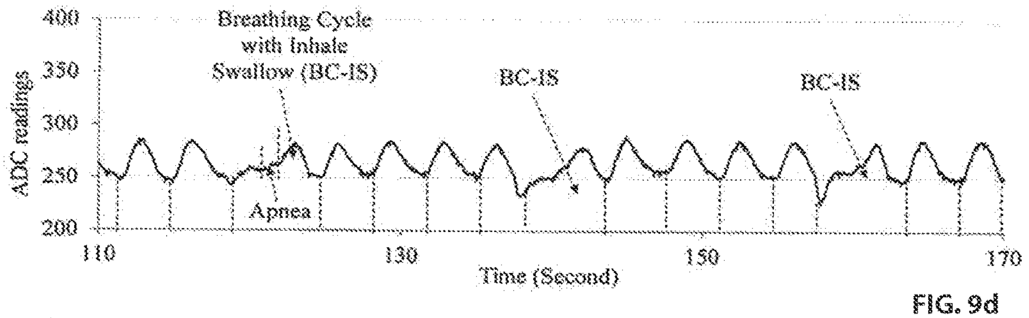
Figure 9D:
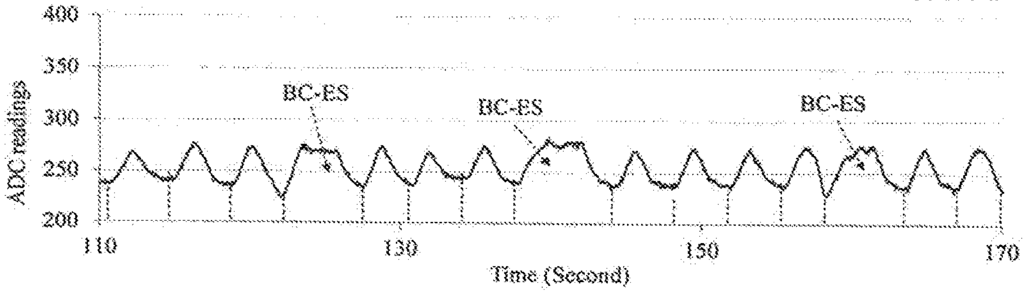
Figure 10A:
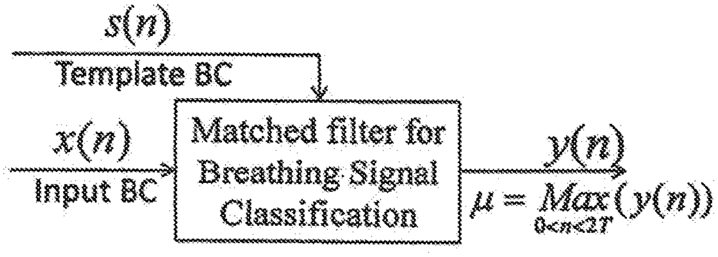
Figure 10B:
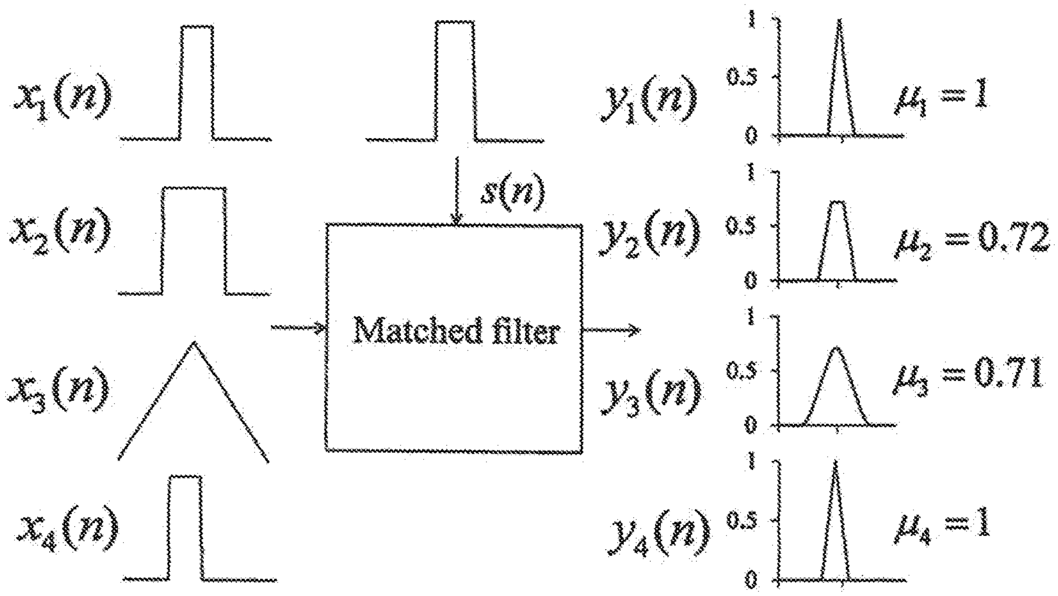
Figure 11A:
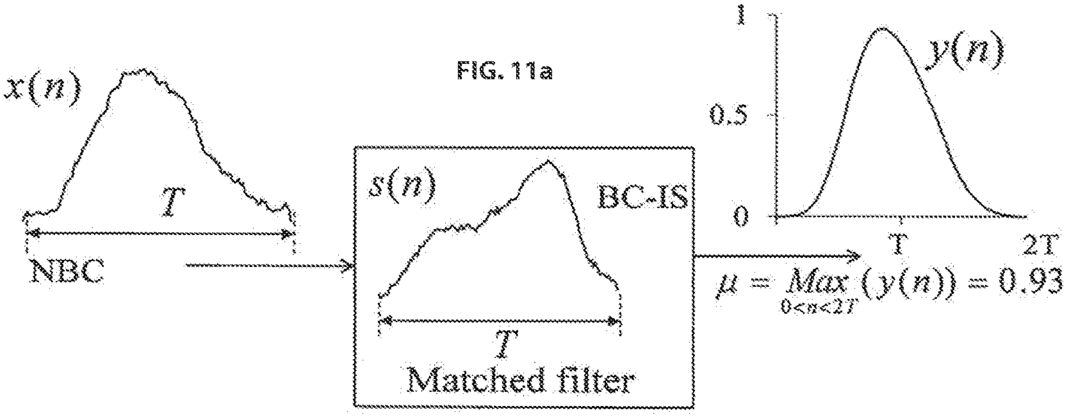
Figure 11B:
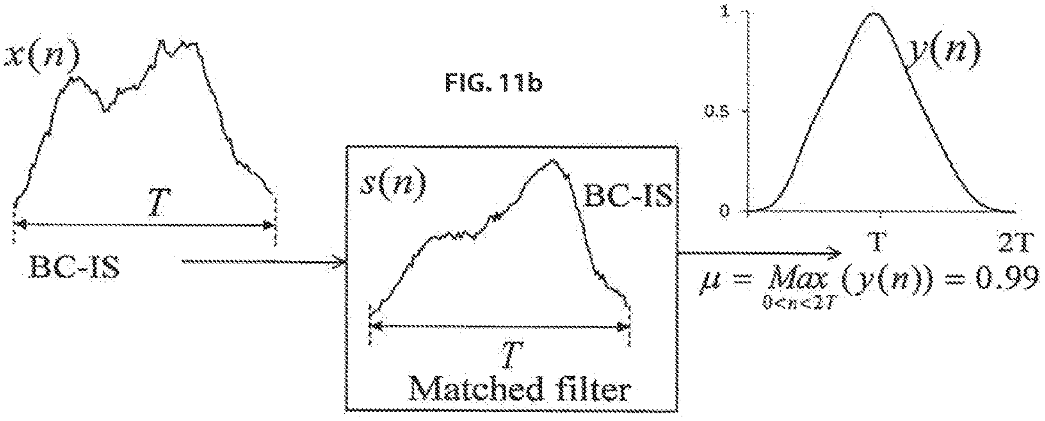
Figure 11C:
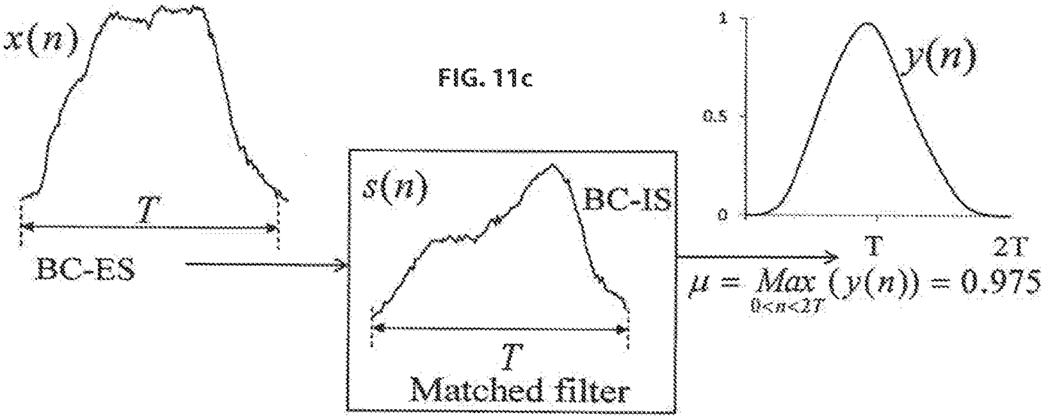
Figure 12:
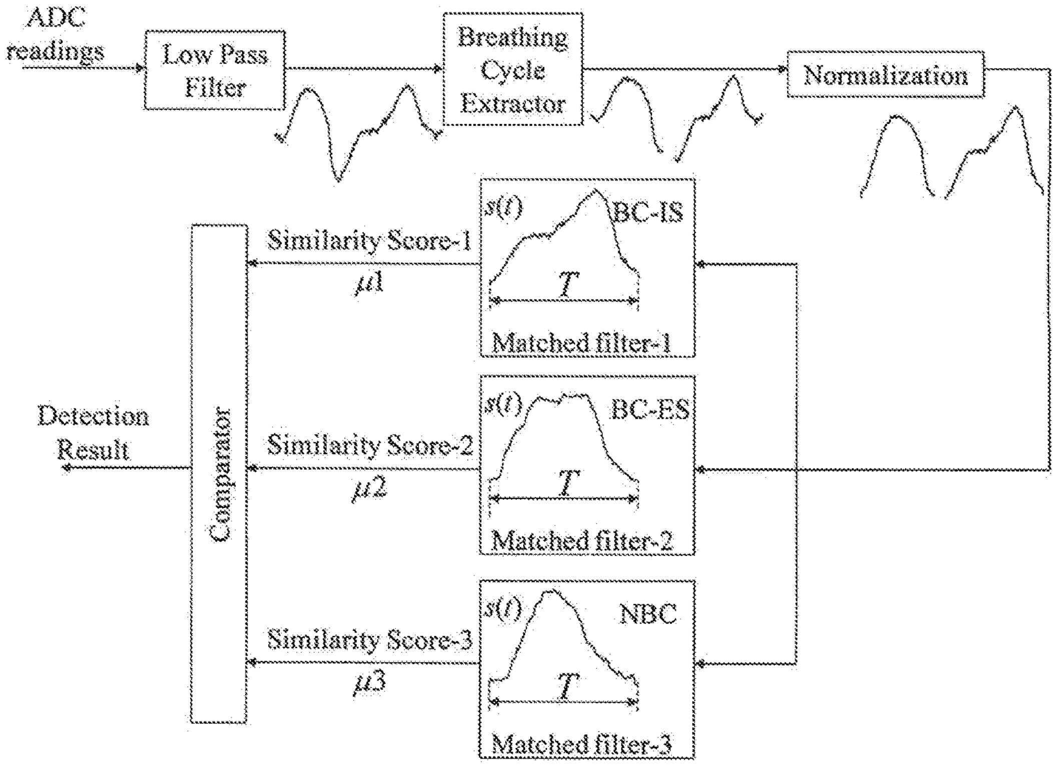
Figure 13A:
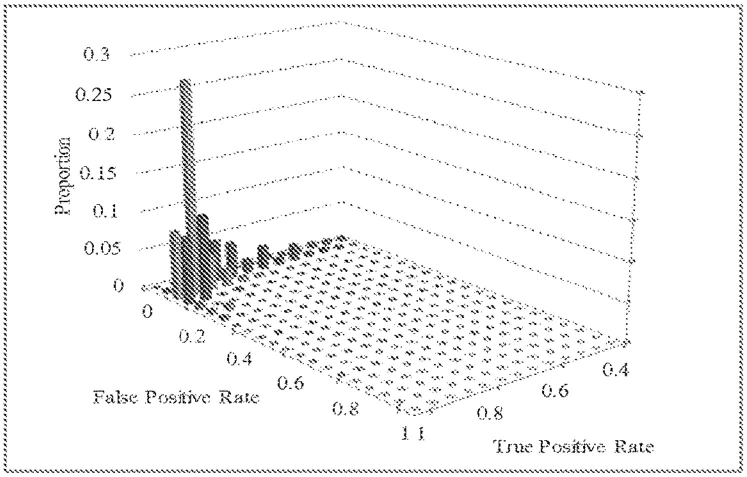
Figure 13B:
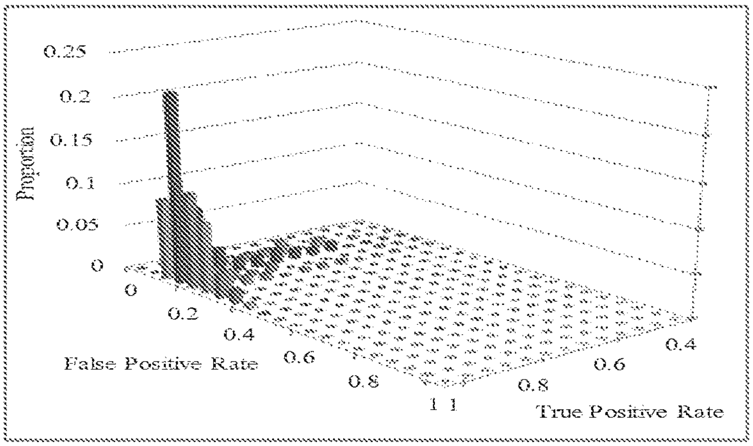
Figure 13C:
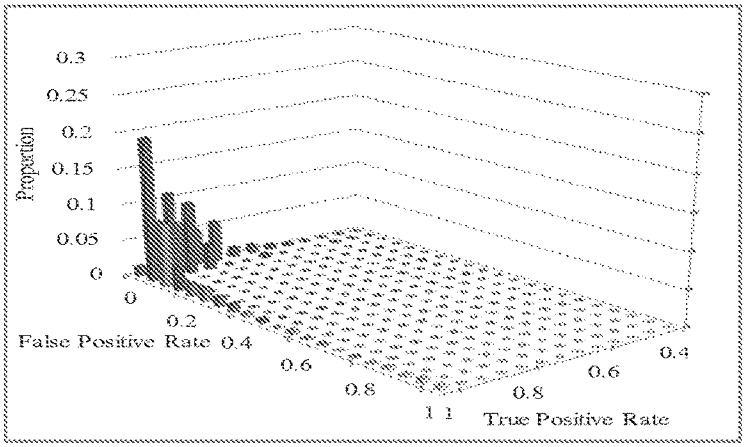
Figure 14:
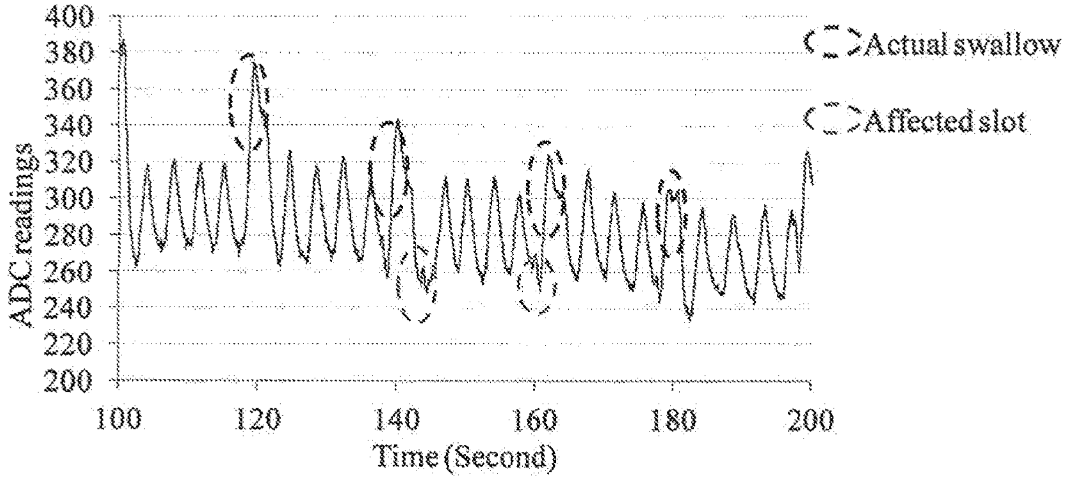
Figure 15A:
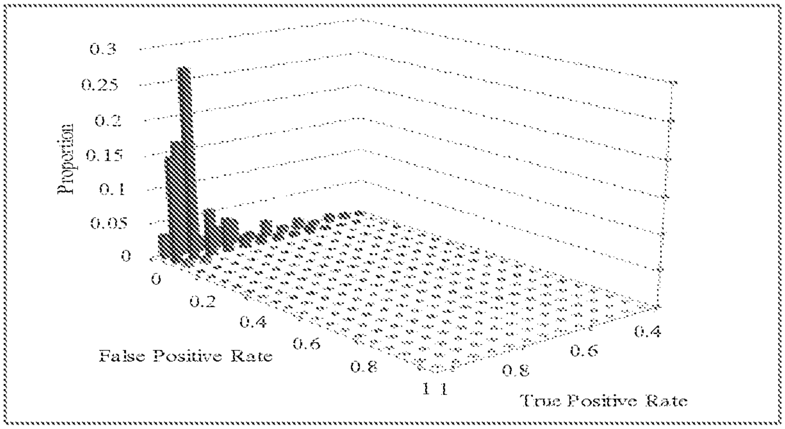
Figure 15B:
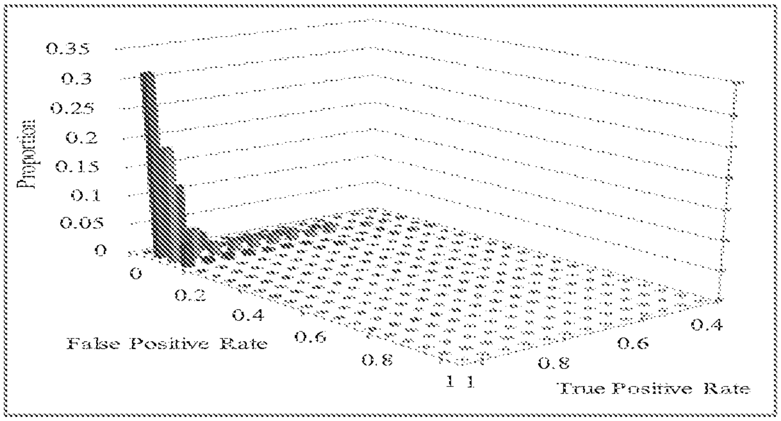
Figure 15C:
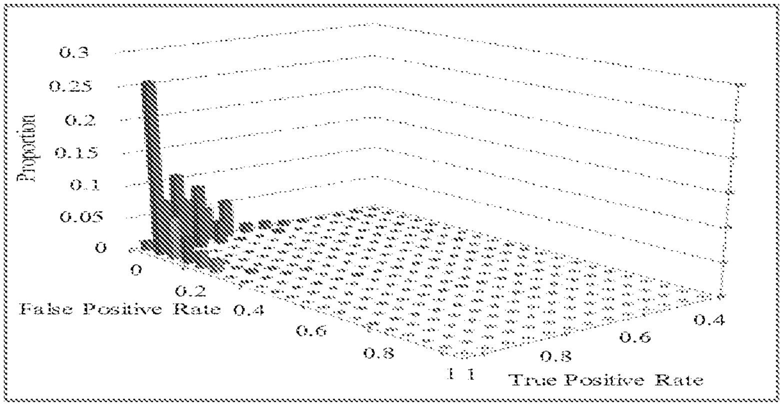
Figure 16A:
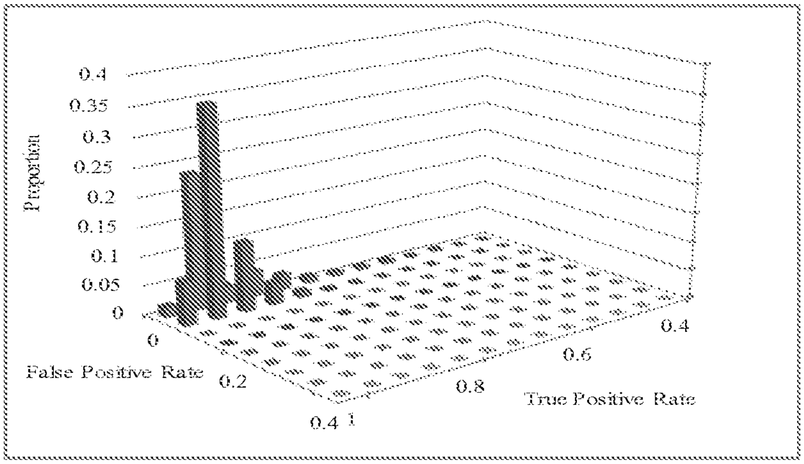
Figure 16B:
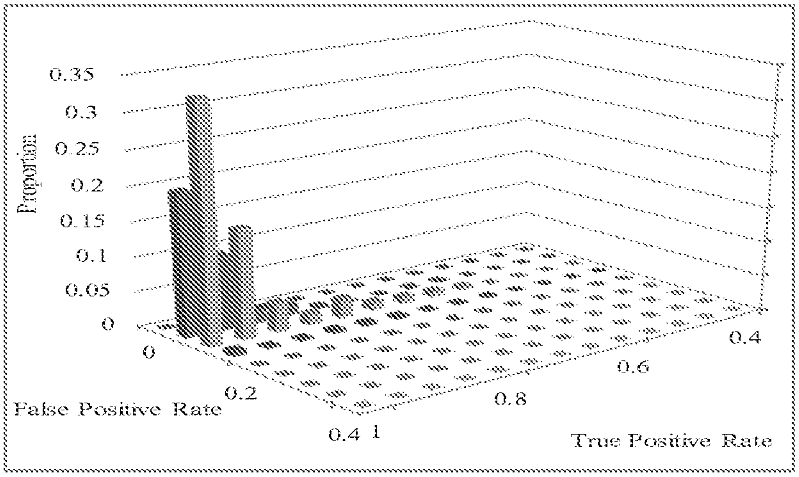
Figure 16C:
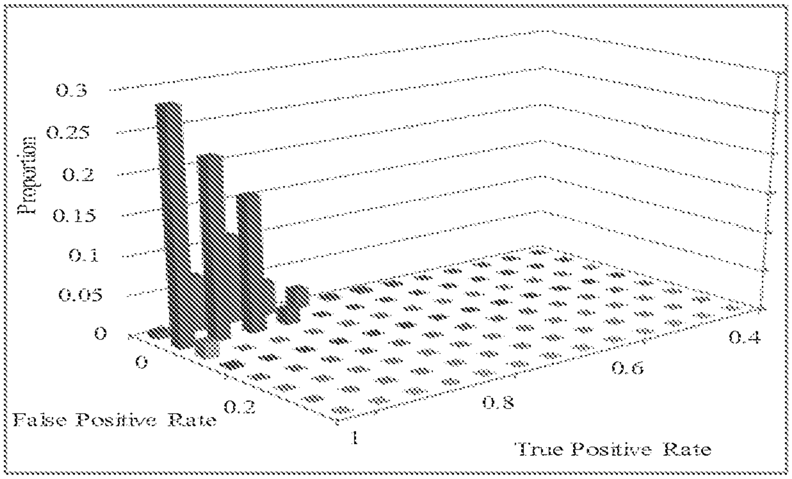
Figure 17A:
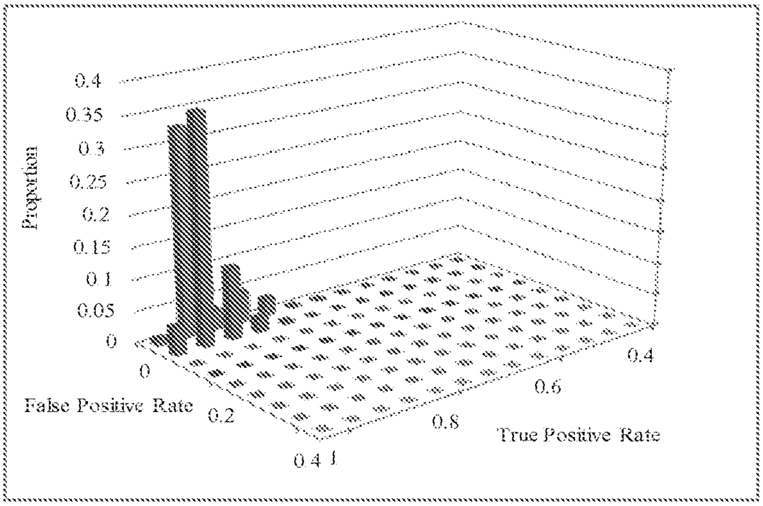
Figure 17B:
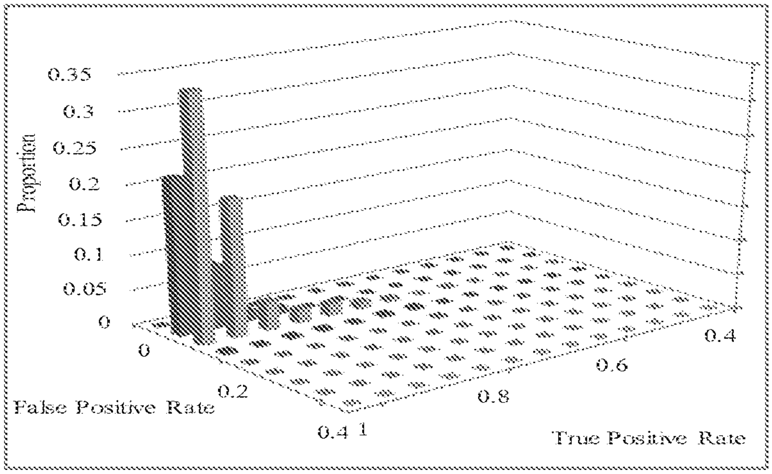
Figure 17C:
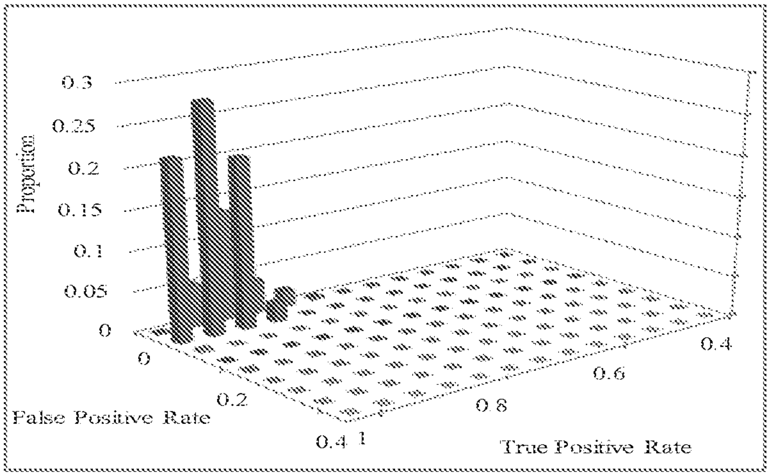
Figure 18:
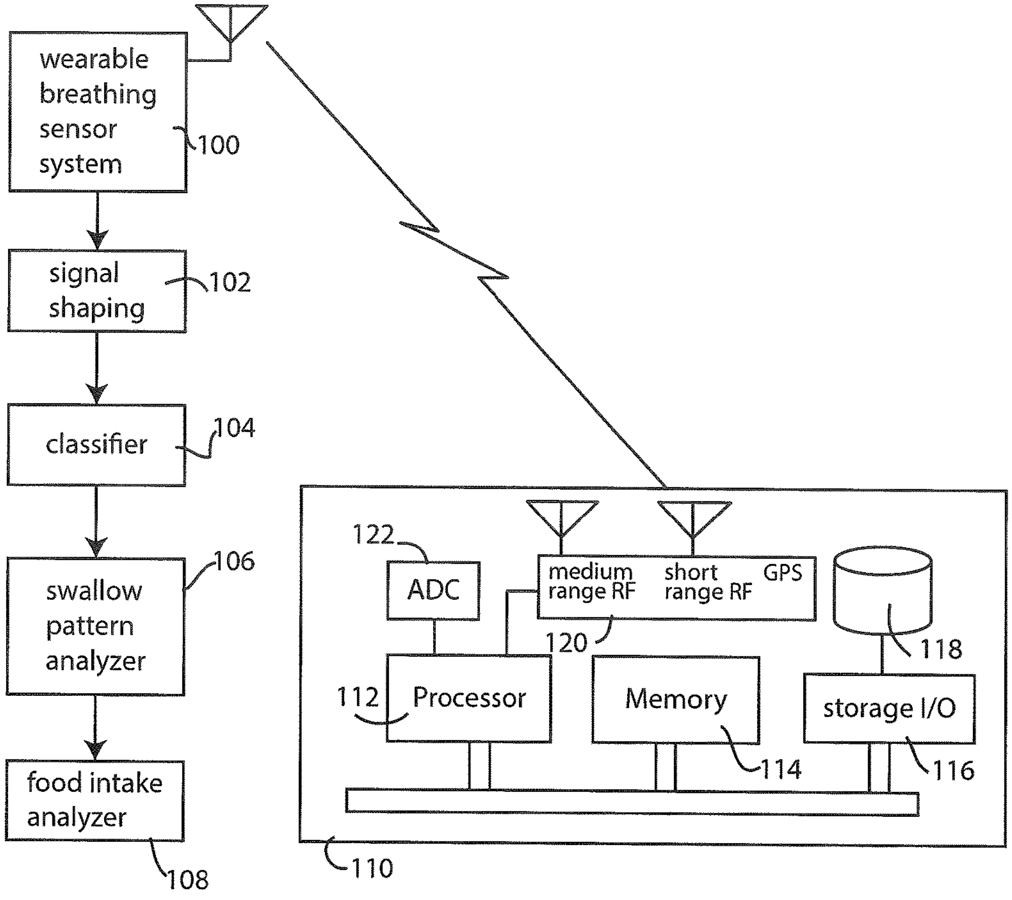
Figure 19:
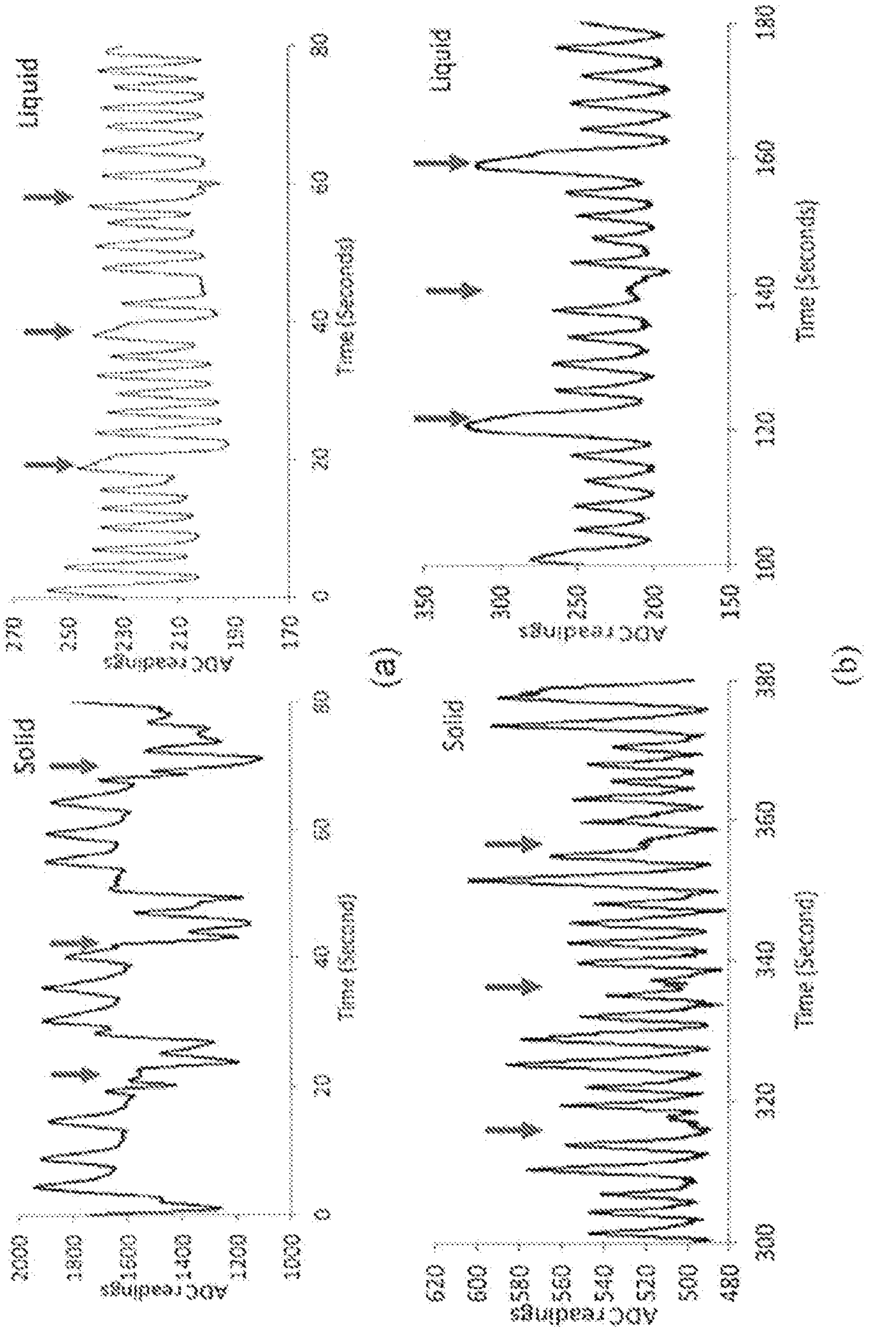
Figure 20:
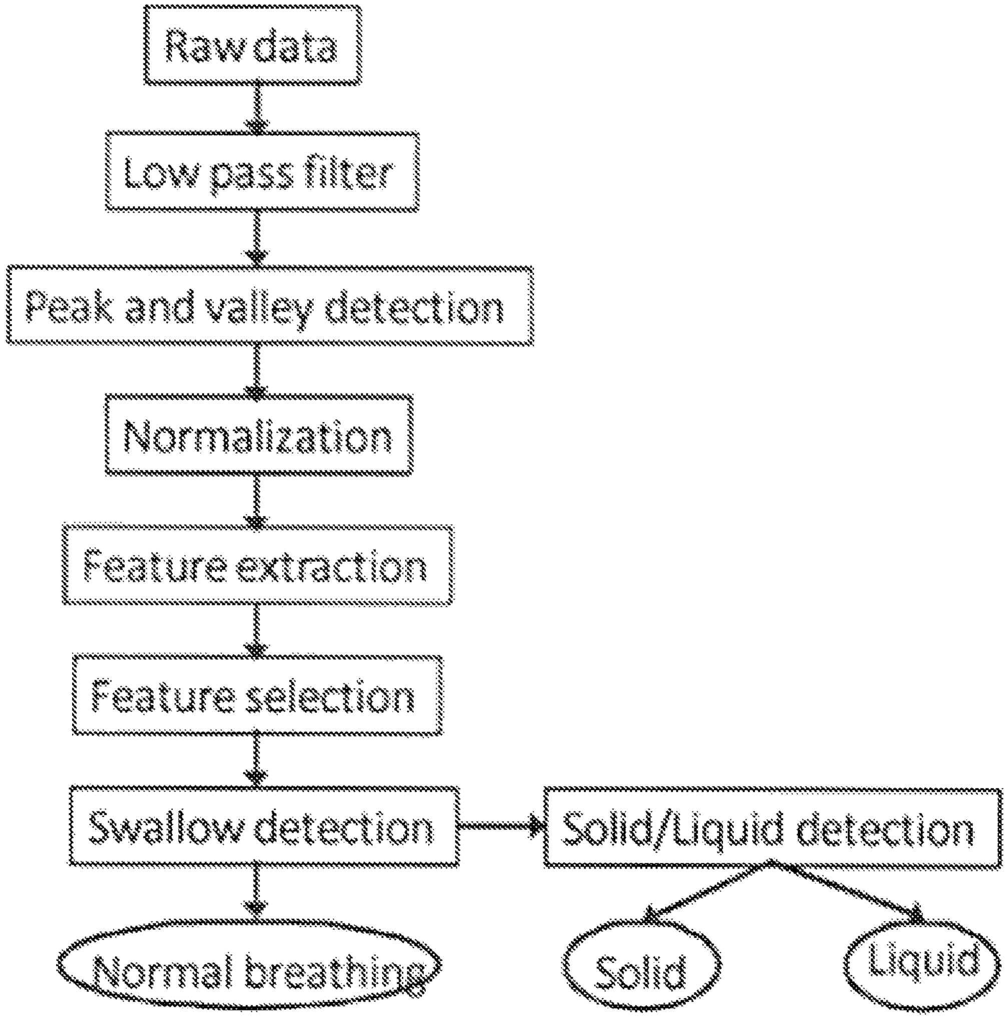

FIGS. 4*a* and 4*b* are graphical diagrams that show the transient response of the resistive belts;

FIG. 5 is a piezo-respiratory belt;

FIG. 6 is a graphical diagram that shows the status response of piezo-respiratory belts;

FIG. 7 is graphical diagram showing the transient response of piezo-respiratory belts;

FIG. 8 is a signal shaping circuit;

FIGS. 9*a*-9*d* (collectively FIG. 9) show examples of respiratory and swallow signals;

FIGS. 10*a*-10*b* (collectively FIG. 10) show the matched filter operation;

FIGS. 11*a*-11*c* (collectively FIG. 11) show and example of BC-IS detection;

FIG. 12 shows the data processing architecture for swallow detection;

FIGS. 13*a*, 13*b* and 13*c* (collectively referred to as FIG. 13) show a receiver operating characteristic (ROC) distribution with arbitrary template selection for different subjects (subject 1, subject 2 and subject 3);

FIG. 14 is a graphical diagram showing examples of BC modulation by adjacent swallows;

FIGS. 15*a*, 15*b* and 15*c* (collectively referred to as FIG. 15) show ROC with breathing cycle modulation removed;

FIGS. 16*a*, 16*b* and 16*c* (collectively referred to as FIG. 16) show ROC with templates formed using two controlled cycles;

FIGS. 17*a*, 17*b* and 17*c* (collectively referred to as FIG. 17) show ROC with templates using three controlled cycles;

FIG. 18 is a system block diagram illustrating one embodiment of a food intake monitoring system in accordance with the disclosed system and method;

FIG. 19 are a collection of graphs providing examples of respiratory and swallow signals, useful in comparing swallowing of liquids vs solids; and FIG. 20 is a data processing scheme for detecting and differentiating swallows of liquids vs. solids.

Corresponding reference numerals indicate corresponding parts throughout the several views of the drawings.

DETAILED DESCRIPTION

Example embodiments will now be described more fully with reference to the accompanying drawings.

The disclosed system and method employs a wearable wireless sensor system for food/drink intake monitoring with an associated computer-implemented analytic framework. The system and method works based on the key observation that a person's otherwise continuous breathing process is interrupted by a short apnea when the person swallows as a part of solid or liquid intake process. Using a wearable wireless chest-belt, the system first detects and records a swallow sequence by detecting the associated apneas extracted from breathing signal captured by the chest-belt. After the swallow sequence is recorded, computer-automated swallow pattern analysis is used to identify non-intake swallows (or empty swallows), solid intake swallows, and drinking swallows. These patterns may then be used to draw inferences about the subject's eating and drinking habits.

One presently preferred embodiment employs swallow detection sensor modality based on piezo-respiratory chest-belts, an embedded hardware and software platform for wirelessly collecting the sensor output, and signal processing mechanisms for swallow detection with high accuracy and low false positives.

In such a presently preferred chest-belt based system, a breathing signal is extracted via monitoring the expansion-contraction pattern of the chest. Since the belt can be worn inside, outside, or between garments (it does not need skin contact), it has the potential for prolonged comfortable usage without raising any cosmetic issues. Extensive experimental evaluation shows the system's robustness in terms of its ability to monitor swallowing by detecting apnea with high accuracy and low false positive rates.

Key Concepts: Breathing, Swallow, and Apnea.

The breathing process is divided into two phases, inhalation and exhalation. Inhalation is initiated by diaphragm and various muscles, leading to the expansion of chest cavity. At the same time, the lungs expand due to the inhaled air through nose (or mouth), throat, larynx, and trachea. Then oxygen is extracted and carbon dioxide is released by pulmonary alveoli. When the exhalation starts, diaphragm and muscles get relaxed, thus pushing air out of lungs through trachea, larynx, throat, and nose (or mouth).

The process of swallowing is normally divided into three phases. When swallow happens, food is first chewed into a bolus (term used for describing a block of food or liquid) and then propelled into the oropharynx by the tongue, which is called the oral phase. In the pharyngeal phase, the palate bocks the back wall of the throat preventing the bolus from going to nasal cavity, and the vocal cords close, blocking the trachea. While the bolus goes down, epiglottis covers the vocal cords, and then the upper esophageal sphincter relaxes allowing the bolus to enter the esophagus. Finally, in the esophageal phase, the bolus enters esophagus and finally arrives at the stomach.

During swallowing, because the trachea is blocked, a person is not able to breath, thus causing a temporary apnea during breathing. A key concept of the proposed system is to extract this apnea as the fingerprint for detecting swallows.

System Architecture.

In one embodiment, an embedded wearable sensor system is worn on the chest for collecting the breathing signal and for transmitting it to a PC or other processing device through a 900 MHz wireless link or access point. In this embodiment the embedded wearable sensor system comprises: 1) a piezo respiratory belt for converting the changes of tension during breathing to a voltage signal, 2) an amplifier and signal shaping circuit for formatting the raw voltage signal to a format compatible for the ADC chip, 3) a processor and radio subsystem (Mica2 motes) running TinyOS operating system, and 4) two AAAA batteries. The entire package is quite lightweight, and the two 600 mAh AAAA batteries are able to support the system for more than 30 hours of continuous operation.

After the signal is received by the 900 MHz access point, it is fed via USB port to a PC (e.g., processing server) for detecting swallowing events in either real time (runtime) or offline. Swallow sequence pattern analysis for food/drink intake estimation is also executed in this external machine (PC). The advantage of using an embedded wireless link is that the developed swallow sensor can be networked with other physiological and physical activity sensors to develop a networked sensing/detection system to provide a complete instrumentation package for obesity management in future.

Of course other processors and radio subsystems can be used. For example, if desired the processing can be performed on a mobile smartphone that communicates with the wearable sensor system via radio communication such as Bluetooth®. In such an embodiment the processor on-board the smartphone performs the data capture and optionally also the data analysis. If desired, the smartphone can communicate either the captured raw data, or preprocessed data, or final analytical results to a server via Wi-Fi™ or cellular communication.

Sensor Selection and Characterization.

This section presents the properties and experimental characterization of different types of chest-belt materials for obtaining respiratory signals in a non-invasive manner. Based on the analysis in this section, a piezo-respiratory belt is presently preferred, although the apnea detection in breathing signal technique disclosed here can also be practiced using other wearable sensor systems, including but not limited to those discussed below.

Inductance Belt.

An inductance belt relies on the phenomenon that a magnetic field is generated when current flows through a loop of wire. Any change in the area enclosed by the loop can create a current in the loop in the opposite direction proportional to the change in the area. While using an inductance belt for respiration monitoring, a low amplitude carrier wave of ~20 mV at ~300 KHz is injected through the loop on the belt. The inhalation and exhalation process change the area enclosed by the belt and introduces an opposing current, which in turn modulates the original carrier wave. The signal is then demodulated to recover a signal that reflects the change of the area due to breathing. It is reported [16] that the output of such belts usually changes linearly with the enclosed cross-sectional area.

Required instrumentation for inductance belts consists of a frequency generator, an analog to digital (ADC) converter, and a signal processing unit. Inclusion of that many active electronic devices make the pricing point of the inductance belts to be currently much higher than the other types of respiration monitoring belts as described below. Future improvements in inductance belt technology may make it cost effective.

Resistive Belt.

Resistive belts use an elastic material whose resistance per unit length depends on the amount of stretch that is created during the breathing process. Resistance change can be easily captured by measuring the voltage drop across the belt. Such belts can be worn either in the abdomen or in the chest area for capturing the expansion-contraction sequence created by the breathing dynamics.

Figure 2:
FIG. 2 is a resistive belt.

We have created a prototype resistive belt using stretch sensors manufactured by Scientific Instruments as shown in FIG. 2. The diameter of the sensor is 1.5 mm, and the length is 15 cm.

Figure 3:
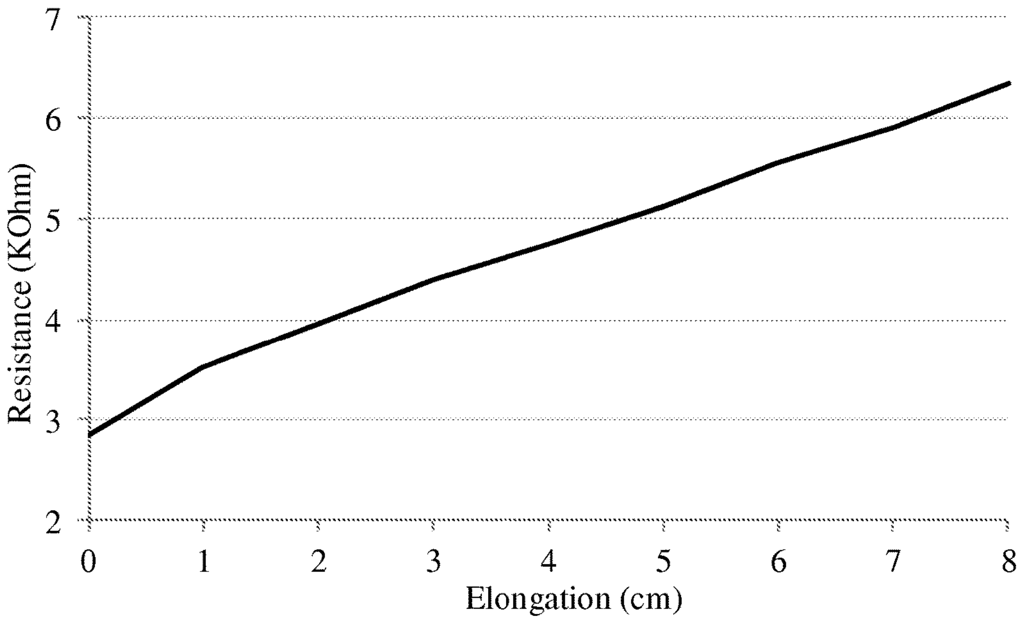
FIG. 3 is a graphical diagram that shows the static response of resistive belts.

Static and transient characteristics of the sensor are analyzed by stretching it to different lengths. FIG. 3 demonstrates the static property of the sensor. In this experiment, the resistance of the sensor at each sample point is read 1 minute after it is stretched so that the impact of transient response is minimized. From FIG. 3, the sensor demonstrates good linearity in static experiments.

To analyze the transient property, the belt is first stretched for 5 cm and kept for 1 minute to make it tight and stable so that the impact of slack is minimized. Then it is stretched by another 5 cm, and the response is recorded. After 1 minute, when the resistance of the sensor becomes stable, it is released by 5 cm. FIG. 4 shows the resistive dynamic response of the belt as a function of time. FIG. 4 (*a*) illustrates the response after it is stretched, and (b) is the response after it is released.

FIG. 4*a* demonstrates that when the belt is stretched, a surge in resistance followed by decay can be observed. FIG. 4*b* depicts that when the belt is released, the resistance surges up a little before decaying to its terminal value. Results above demonstrate that although the static behavior of the resistive belts maintain excellent linearity, their transient behavior is highly non-liner over time constants that are comparable to human breathing periods. As a result, despite their cost advantages current resistive belts are not considered as the best sensing tool for the swallow detection mechanism presented in this work. Future improvements in resistive belt materials may produce better linearity over time constants comparable to human breathing periods. In such case, resistive belts may become suitable for detecting apnea in breathing signals.

Piezo-Respiratory Belt.

A piezo-respiratory belt contains a piezoelectric sensor placed between two elastic strips. Stretching the belt exerts a strain on the sensor, which generates a voltage proportional to the strength of the force. Comparing with other transduction principles, such as capacitive, inductive and piezoresistive effects, piezoelectric phenomenon currently provides the highest sensitivity and excellent linearity over a wide amplitude range.

FIG. 5 shows the piezo-respiratory belt from ADI Instruments used in a presently preferred system. The static response of the belt is shown in FIG. 6, which demonstrates good linearity of produced voltage as a function of belt elongation.

FIG. 7 demonstrates the voltage signal captured by oscilloscope when the piezo-respiratory belt is first stretched by 15 mm and then released after some time. It is notable that unlike in the transient response of the resistive belt in FIG. 4, the output of the piezo-respiratory belt closely follows the mechanical inputs (i.e. stretch and release) without the surges. It is because of its static response and clean transient response we chose the piezo-respiratory belts for our presently preferred swallow detection system. Of course, as noted above, as materials improve, other types of sensors may become useful in the future.

Signal Shaping Hardware.

The voltage output from the piezo-respiratory belt is shaped as follows. First, the voltage output from the belt needs to be amplified since the peak-to-peak voltage variation during inhale-exhale cycle is only 10 mV which is smaller than what majority of the off-the-shelf ADC converters can discern with acceptable accuracy. Second, depending on the wearing tightness of the belt there is a DC component in the output voltage, which can vary from person to person depending on how tightly the belt is worn. Sometimes the DC component can even vary for the same person on different wearing instances. The situation is further aggravated when the DC value changes over time as the belt becomes loose after a subject wore it for some time. The shaping circuit thus needs to take care of such person-, wearing-, and time-dependent variability of the DC component of the output voltage from the piezo-respiratory belt.

Figure 1:
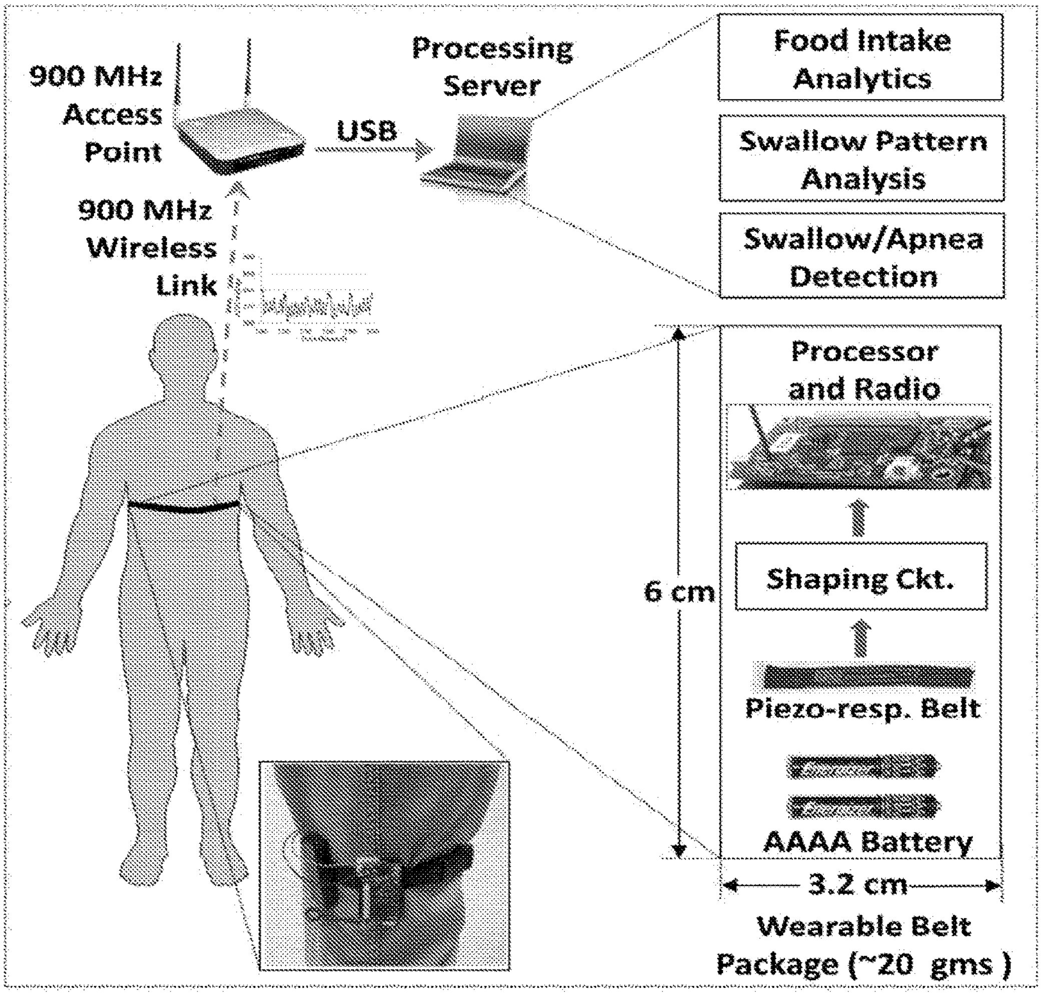
FIG. 1 is a wearable wireless food intake monitoring system.

The shaping circuit shown in FIG. 8 serves the above shaping needs by first removing any DC voltage component (i.e. low pass filter) in the signal, and then by amplifying the AC-only signal which is fed into the analog-to-digital convertor (ADC) of the processor and radio card as shown in FIG. 1.

The shaping circuit in FIG. 8 has six distinct stages, although other types of shaping circuits may alternatively be used. The first stage represents the equivalent circuit of the piezo-electric sensor device which contains a voltage generator and a capacitor. The second stage is a drift-control module which is meant for damping DC voltage drifting when the belt is worn by different subjects. The third stage is for voltage shifting. It sets the default DC voltage to be 63 mV, so that the output signal always stays positive. The fourth stage is for impedance matching by isolating the previous stages of the signal shaping circuit from the amplification stage. The fifth stage is a low-pass filter that filters out any noise produced by the previous stages. Finally, the sixth stage is the amplifier, whose amplification gain is controlled by an adjustable resistor.

The output of the shaping circuit as depicted in FIG. 8 is fed into a 10-bit ADC channel of a processor and radio card in FIG. 1. With a 3V power supply (i.e. two AAAA batteries) the resolution of the 10-bit ADC is 3 mV. ADC sampling rate is set to be 30 Hz. As shown in FIG. 1, the collected data is sent wirelessly to an access point via 900 MHz radio link. The access point feeds the data to a processing server machine for executing the swallow detection algorithms.

Breathing Signal and Apnea Analysis.

FIG. 9 demonstrates a number of experimentally obtained breathing signal segments from different human subjects using the system as shown in FIG. 1. The ADC readings in the figure are directly proportional to the tension on the piezo-respiratory belt, meaning the rising edge in the graph corresponds to inhalation and the falling edge corresponds to exhalation of a breathing cycle.

As shown in FIG. 9 a breathing cycle can be either normal (i.e. NBC) or elongated due to a momentary apnea caused due to a swallow event. A cycle that is elongated due to an apnea at the beginning of an exhale (see FIG. 9*a* for subject-1, session-1) is termed as Breathing Cycle with Exhale Swallow (BC-ES). Both FIG. 9*a* and FIG. 9*b* depict BC-ES events recorded for subject-1 in two different sessions. For a second subject, FIG. 9*c* shows swallows (i.e. apnea) during the inhale process which are termed as Breathing Cycles with Inhale Swallow (BC-IS). The same second subject was instructed to perform BC-ES during a second session as presented in FIG. 9*d*.

One key objective of the disclosed system is to classify the three types of breathing cycles, namely, NBC, BC-ES, and BC-IS, with high accuracy and low false positive rates. The challenges in this task stem from the fact that there are significant amounts of variability in: 1) breathing waveforms across different subjects, 2) across different measurement instances for the same subject, and 3) most importantly, the placement and duration of the apnea with respect to its home breathing cycle. This depends a great deal on the swallowing habits and the specific material (i.e. solid, liquid, etc.) that is being swallowed. During the course of our experimentation with a large number of subjects and multiple sessions with each subject, it was found that the majority of swallow-triggered apneas were found to have happened either in the middle of the inhale or right at the beginning of the exhale as shown in FIG. 9.

Processing for Swallow Detection.

This section introduces a matched filter based template matching mechanism for swallow detection.

Matched Filter.

In one presently preferred embodiment a matched filter is used for detecting the presence of a known signal, referred to as template, by correlating the template signal with an unknown signal. In this embodiment, the template signal is chosen from different types of breathing cycle waveforms, namely, Normal Breathing Cycle (NBC), Breathing Cycle with Exhale Swallow (BC-ES), and Breathing Cycle with Inhale Swallow (BC-IS), so that the an arbitrary breathing cycle can be classified as one of those three by observing the similarity score produced by the matched filter.

As shown in FIG. 10*a*, the matched filter in this context is parameterized by input x(n) and template s(n), representing waveforms corresponding to a single breathing cycle consisting of T samples (i.e. $0<n<T$). Note that the durations of both the waveforms are assumed to be equal. The output of the matched filter is represented as y(n) which consists of 2T samples. Finally, the similarity score of the filter is parameterized as p, which is the highest value of y(n) over the interval $0<n<2T$.

Output of the filter y(n) is computed as time delayed convolution:

$$y(n) = \sum_{k=-\infty}^{+\infty} x(k)h(n-k)$$

where $h(n)=s(T-n)$ is the impulse response of the filter for a given template s(n). As the similarity between input x(n) and template s(n) becomes stronger, the amplitude of the output y(n) increases, thus producing larger similarity score $\mu$. Since the quantity $\mu$ is computed as the highest value of y(n) over the interval $0<n<2T$, the impact of time shift between x(n) and s(n) is removed.

FIG. 10*b* shows an example operation of matched filter. The figure shows four operation instances with different input waveforms $x_k(n)$ (k=1, 2, 3, 4) but with the same template waveform. Observe that $x_1$ (n) is same as the template waveform without any time-shift, $x_2$ (n) and $x_3$ (n) are different from the template, and $x_4(n)$ is derived by time-shifting $x_1(n)$. The waveforms $y_k(n)$ are the outputs of the filter for each of the corresponding $x_k(n)$. Note that the similarity $\mu_1$ and $\mu_4$ are equal to 1, which are greater than $\mu_2$ and $\mu_3$. This is because $x_1(n)$ and $x_4(n)$ share the same shape of reference template fed into the filter. The impact of time shifting (i.e. from $x_1(n)$ and $x_4(n)$) is removed by selecting the maximum value of y(n) as the similarity score.

FIG. 11 depicts example matched filter operations with a Breathing Cycle with Inhale Swallow (BC-IS) as the template input. Observe that in FIG. 11*a*, when the input to the filter is a Normal Breathing Cycle (NBC), the output $\mu$ is 0.93, which is smaller than the output (i.e. 0.99) in FIG. 11*b* in which the input is a BC-IS waveform. The output is smaller (i.e. 0.975) in FIG. 11*c* in which the input is a BC-ES waveform. This example shows how the matched filter is able to produce a higher output when the input is of the same breathing cycle type as the template waveform, even though the specific BC-IS input waveform in FIG. 11*b* is different from the actual template waveform. Similar behavior was also recorded when NBC and BC-ES waveforms were used as template waveforms.

Processing Architecture.

FIG. 12 depicts the processing modules used for classifying breathing cycles towards swallow detection. The first step is to pass the ADC output through a low-pass filter for removing quantization caused by the A-to-D conversion process. The second step is to run the filtered data stream through a peak and valley detection module in order to extract the individual breathing cycles. The next processing module is used for normalizing the extracted cycles in both time and amplitude dimensions. The objective of such normalization is to make sure that although different cycles may have different time and amplitude ranges (person-to-person or cycle-to-cycle for the same person) they can be effectively correlated for the template matching purposes. In other words, the normalization process ensures that both x(n) and s(n) waveforms are of same duration (i.e. T samples).

The normalized breathing cycle waveforms are then fed into three separate matched filters, each with a specific type of reference template waveform. The matched filters use reference waveforms corresponding to normal breathing cycle (NBC), Breathing Cycle with Exhale Swallow (BC-ES), and Breathing Cycle with Inhale Swallow (BC-IS), as shown in FIG. 9. The similarity score output of all three filters are finally compared to classify a breathing cycle waveform as one of the above three types of BCs.

Performance.

Extensive experiments using the system in FIG. 1 were carried out for swallow detection with seven subjects. Results for three male subjects are presented in this section.

Experimental Method.

Each subject performed three sessions, five minutes each. The subject was asked to wear the instrumented chest-belt and drink water from a flask with a swallow instruction given once in every 20 seconds. Each session resulted in approximately 80 Normal Breathing Cycle (NBC) and approximately 15 breathing cycles with swallows (both Breathing Cycle with Exhale Swallow (BC-ES) and Breathing Cycle with Inhale Swallow (BC-IS)). The resulting swallow signals are collected over the 900 MHz wireless link as shown in FIG. 1. For each session, approximately 90 breathing cycles are recorder in total.

A small microphone was also attached to the front part of the neck for recording the swallow sound. This audio signal, which was time-synchronized with swallow data extracted from the chest-belt, provided a control that was used for both training and verification of the proposed swallow detection mechanism. Two male and one female subject performed the above procedure.

TABLE 1

Breathing cycle breakdown

| | NBC (%) | BC-ES (%) | BC-IS (%) |
|---|---|---|---|
| Subject 1 | 81.10% | 13.40% | 5.50% |
| Subject 2 | 81.80% | 17.40% | 0.80% |
| Subject 3 | 81.80% | 18.20% | 0 |

Breathing Cycle Statistics.

Table 1 summarizes the breakdown of different types of breathing cycles observed during these experiments. For these three specific and other subjects it was consistently observed that Breathing Cycles with Exhale Swallow (BC-ES) are generally more prevalent than Breathing Cycles with Inhale Swallow (BC-IS). In other words, most instances people swallow immediately after inhalation followed by exhalation.

TABLE 2

Durations of different breathing cycle types

| | | NBC (Seconds) | BC-ES (Seconds) | BC-IS (Seconds) |
|---|---|---|---|---|
| Subject 1 | Maximum | 4.93 | 7.36 | 7.34 |
| | Minimum | 1.63 | 2.7 | 2.58 |
| | Average | 3.46829 | 5.710313 | 5.491538 |
| Subject 2 | Maximum | 5.75 | 7.54 | 4.95 |
| | Minimum | 1.63 | 3.85 | 2.28 |
| | Average | 3.46396 | 5.146047 | 3.615 |
| Subject 3 | Maximum | 4.97 | 6.58 | None |
| | Minimum | 1.86 | 3.73 | None |
| | Average | 3.406763 | 4.984667 | None |

Table 2 summarizes the duration of different types of breathing cycles. In addition to the spread of the cycle durations, it should be observed that the cycles with swallows (i.e. both BC-ES and BC-IS) are consistently longer than the normal breathing cycles. This is mainly due to the short apnea introduced by the swallow events.

Performance Parameters.

The system performance is reported as ROC (Receiver Operating Characteristic) statistics of True Positive Rate vs. False Positive Rate. These two rates are computed using performance indices as reported in Table 3. True Positive Rate is defined as the number of correctly detected BC-IS and BC-ES as a fraction of the total number of BC-IS and BC-ES. This can be expressed as TP/(TP+FN). False Positive Rate is defined as the number of erroneously detected BC-IS and BC-ES as a fraction of the total number of NBCs.

TABLE 3

Detection performance indices

| Term | Explanation |
|---|---|
| TP (True Positive) | No. of correctly detected BC-IS and BC-ES |
| FP (False Positive) | No. of erroneously detected BC-IS and BC-ES |
| TN (True Negative) | No. of correctly detected NBC |
| FN (False Negative) | No. of undetected BC-IS and BC-ES |

Arbitrary Template Waveforms.

As a first step, we have evaluated the system's detection performance with arbitrary combinations NBC, BC-IS and BC-ES waveforms as the reference input s(t) as shown in FIG. 12. The evaluation process is as follows.

First, for each subject, approximately 3500 different reference combinations of NBC, BC-IS and BC-ES waveforms are created from approximately 300 breathing cycle waveforms collected from three experimental sessions. Second, for each reference combination, all 300 breathing cycle waveforms are detected to be one of NBC, BC-IS and BC-ES using the system described herein. Third, by comparing these detection results with the actual breathing cycle types observed from the neck-attached microphone for all 300 cycles a True Positive Rate and a False Positive Rate (from the parameters in Table 1) are computed. Using the above process an ROC pair (True Positive Rate, False Positive Rate) is computed for each of the 3500 reference combinations. FIG. 13 shows the ROC (True Positive Rate, False Positive Rate) distribution of 3500 such pairs for three different subjects.

The following observations can be made from FIG. 13. First, the cluster of high value columns in the diagram indicate that even with arbitrarily chosen template waveform combinations, majority of the combinations offer high True Positive Rate and low False Positive Rate. The spread in the distribution indicate that there exist NBC, BC-IS, and BC-ES waveforms which, if chosen as templates, can indeed bring down the system performance. As a result, this approach of random template selection is not practically feasible. The task of appropriate template selection will be dealt with in the following sections.

Breathing Cycle Modulation by Adjacent Swallows.

It was experimentally observed that sometimes a swallow event in a breathing cycle can modulate the signal for cycles that are immediately before or after. Such modulations are demonstrated in the example trace in FIG. 14. It was determined that most of the affected cycles before actual swallows were caused by a minor change of breathing in subconscious anticipation of an impending swallow. The affected slots after actual swallows were caused due a similar reason. The subjects also reported that sometimes they executed and very minor second swallow for drinking any remaining liquid in the throat region.

It turns out that the matched filter based system is often able to detect the above modulation and reports such occurrences as two swallows in consecutive breathing cycles, thus contributing to the false positive rate. Given that such modulations by adjacent swallows are always involuntary, it is reasonable to filter them out. Considering that it is extreme rare for people to have real swallows in consecutive cycles, we count any two swallows that happen in consecutive breathing cycles as one.

FIG. 15 reports the ROC distribution when the above filtering scheme is applied to the results obtained from FIG. 13. As expected, filtering out the breathing cycle modulation does reduce the false positive rates while maintain the true positive rates as obtained in the without filtering scenario. Unless otherwise stated, all subsequent results in the paper correspond to this modulation filter enabled.

Globally Averaged Template Waveforms.

Results in this section correspond to a detection scenario in which for a given subject, all normalized NBC waveforms are averaged on a sample-by-sample basis to create the reference template for the NBC filter. Similarly, all normalized BC-IS and BC-ES waveforms are averaged for the creating the templates for the BC-IS and BC-ES filters respectively. This arrangement is expected to provide a best case performance indication of the system. Table 4 summarizes the detection performance with such globally averages template waveforms.

TABLE 4

Performance with globally averaged templates

| | True Positive Rate | False Positive Rate |
|---|---|---|
| Subject 1 | 0.933 | 0 |
| Subject 2 | 0.933 | 0.089 |
| Subject 3 | 0.911 | 0.010 |

While providing a performance upper bound, this mechanism of template formation is not practically feasible since the breathing cycles need to be classified a priori in order to prepare the templates themselves. The next two sections details two practically feasible detection mechanisms.

Template Formation Using Controlled Breathing Cycles.

Results in this section correspond to template waveforms that are computed based on average of known cycle types during a brief controlled phase. At the beginning of data collection for each subject, a number of NBC, BC-IS, and BC-ES cycles are recorded on instruction. Meaning, data recorded from each such cycle, referred to as controlled cycle, is known to be of its specific type. After the control phase, a sample by sample average NBC waveform is created from the recorded controlled cycles of type NBC. This average waveform is used as the template for the NBC matched filter. Templates for BC-IS, and BC-ES filters are computed using the controlled cycles of the respective types. Unlike the globally computed average, this mechanism can be practically feasible.

FIG. 16 reports detection performance using two controlled cycles. To capture the effects of variability present in the controlled cycles, for each cycle type we arbitrarily choose two breathing cycles from the entire pool of collected cycles, and use them as the controlled cycles. We compute the true positive and false positive rate for each such combination of two controlled cycles for three cycle types. A distribution of 3500 such combinations is reported in FIG. 16.

As expected, the performance distribution in this case shows relatively better true and false positive performance compared to those corresponding to single arbitrarily selected template.

FIG. 17 reports the case when 3 controlled cycles are used for creating the reference waveforms for the matched filters. Comparing with FIG. 16 it can be observed that the overall performance is further improved which is indicated by stronger clustering of the histogram columns near 0% false positive rates and 100% true positive rates.

Discussion of Additional Embodiments

While the system and method of food intake monitoring using apnea detection in breathing signals can be implemented in a variety of different ways, refer now to FIG. 18, which shows one way of implementing such a food intake monitoring system. In accordance with the description above, the system employs a wearable breathing sensor system 100. In a presently preferred embodiment this wearable breathing sensor system may be a piezo-respiratory belt, although other types of sensors could be used instead.

Depending on the sensor system selected, a signal shaping circuit 102 is employed, to bring the raw signal levels of the sensor system up to a useable voltage and to filter out any DC component or unwanted noise components in the raw signal. In this regard, the primary function of the breathing sensor system is to obtain measurement data from which the wearer's breathing patterns may be analyzed. Thus the raw signal from the breathing sensor system may be filtered, as discussed above to filter out signal information that is not varying over a period commensurate with the expected period of the human breathing cycle.

As described above, the presently available sensors that are suitable for sensing human breathing patterns produce analog outputs. Thus the signal shaping circuit 102 may be implemented, as shown in FIG. 8 as an analog signal processing circuit. Alternatively, signal processing of the raw sensor output can be performed in the digital domain. In such case the raw sensor output is digitized using a suitable analog-to-digital convertor to sample the analog sensor output and thereby produce digital data indicative of the measured breathing patterns.

Once the raw signals have been processed to put them into a useable, standardized form, they are then fed to the classifier 104 which functions to classify intervals of the measured breathing patterns according to predefined categories. In the presently preferred embodiment the classifier is configured to classify breathing patterns into one of three types, namely NBC (normal breathing cycle), BC-ES (breathing cycle with exhale swallow, and BC-IS (breathing cycle with inhale swallow). These three types are discussed more fully above, and are used in the presently preferred embodiment to extract information from which the wearer's eating and drinking behavior can be inferred through data analysis.

In the illustrated embodiment featured in FIGS. 10-12, the classifier was implemented as a set of matched filters. These filters can be constructed to operate in the analog domain, or in the digital domain, depending on the implementation. The classifer 104 may also be implemented using a trained stochastic, statistical, neural network or probabilistic model if desired. In such an embodiment the model may be trained using examples of known breathing patterns (NBC, BC-ES and BC-IS) to define a set of classifiers, one tuned to recognize each of the breathing patterns.

In operation, classifier 104 provides as its output a detection result, typically an indication of which breathing pattern was recognized. In this regard, because human breathing is basically cyclic, the classifier may be configured to parse the raw data into inhale-exhale cycles, and then operate upon each cycle individually to classify it. In practice this is preferably done by supplying the inhale-exhale cycle data to each classifier (that is, to the NBC classifier, the BC-ES classifier and the BC-IS classifier), allowing each classifier to generate an output reflective of how closely the input cycle matches the breathing cycle it is designed to recognize. If desired each classifier may also output a similarity score that serves as a measure of how likely each classifier has performed its recognition task. Thus if the NBC classifier outputs a 98% likelihood score, and the BC-ES and BC-IS classifiers output 12% and 21% scores, respectively, the system can safely conclude that the breathing pattern being examined is an NBC pattern. In the case where there is no clear winner, the results of analysis for that breathing cycle may be discarded as unreliable.

As the classifier 104 produces its output, in the form of a string or sequence of NBC, BC-ES and BC-IS classifications for individual breathing cycles, this sequence is fed to the swallow pattern analyzer 106. The swallow pattern analyzer performs a computational analysis upon the breathing patterns to extract inferences as to whether the wearer is eating or drinking, and also in some cases what the wearer is eating or drinking. The swallow pattern analyzer may be implemented using a computer or processor that has network communication capability so as to receive geolocation data as well as date and time data. By associating swallow patterns with date and time of day and with geolocation, a record of when and where the wearer was eating or drinking. The swallow pattern analyzer may be based on a trained model, using pattern recognition techniques discussed above, to classify different swallowing sequences as corresponding to the eating and drinking of different foods or beverages. The pattern recognizer can be trained in use so that it learns over time what a particular food or beverage looks like in terms of swallow patterns. Training may be supervised by tying the swallow pattern analyzer to a food intake analyzer 108 that includes a suitable user interface through which the wearer logs in what he or she has eaten at each meal. The recognizer is trained by correlating the entered food and beverage items to different swallow patterns, so that over time the swallow pattern analyzer becomes able to distinguish between eating a bag of French fries and eating a carrot stick.

The subsystems that make up the food intake monitoring system described in FIG. 18 can be implemented in a variety of ways. In some embodiments many of the components can be embedded in the wearable breathing sensor belt; in other embodiments some of the components may be incorporated into a portable device carried by the wearer of the sensor belt; in still other embodiments some of the components may be remotely located and accessed by network or telecommunication link, such as by Wi-Fi™ connection to a server located on the Internet. Thus the distribution of components illustrated in FIG. 18 can be deployed in a variety of different configurations.

In one embodiment, the wearable breathing sensor system communicates by a wireless link, such as by Bluetooth®, to a mobile device such as a smartphone 110. The smartphone includes at least one processor 112 that performs program instructions to implement some or all of the system components 102-108. These program instructions are loaded and operated in memory 114 as an App, or as a Web-based application. The smartphone 110 further includes a storage input/output subsystem 116, which includes onboard storage 118, such as flash memory 118, where the App may be stored and also where data obtained by the food intake monitoring system may be stored. The smartphone 110 also includes a radio communication system 120 that preferably includes support for short range RF Bluetooth® communication, mid range RF Wi-Fi™ communication and optionally cellular communication, as well as GPS receiver equipment to provide geolocating services.

In most cases, it is less taxing on the battery resources of the smartphone to digitize the raw signals obtained from the wearable breathing sensor system 100 before they are sent via Bluetooth® to smartphone 110. However, if desired, the smartphone can be equipped with analog-to-digital conversion circuitry 122, allowing the raw analog data to be sent and processed within the smartphone or by equipment attached to the smartphone.

The signal shaping 102, classifer 104, swallow pattern analyzer 106 and food intake analyzer 108 functionality can be performed by the processor 112 onboard the smartphone 110. However, if desired some of the computationally intensive tasks may be offloaded to a server with which the smartphone communicates by wireless network connection.

It will of course be appreciated that even using a smartphone or other portable device there is still wide variation in how a particular embodiment may be deployed. Thus, while the foregoing has placed most of the computational tasks on the processor of the smartphone, other division of labor is also envisioned. Thus, for example, the signal shaping 102 functionality may be deployed on the wearable belt device, or on a small system attached to the wearable belt device. Also, for example, portions of the functionality of the classifier 104, swallow pattern analyzer 106 and food intake analyzer 108 can be performed on processor 112, with other portions of that functionality being distributed to other processors via network communication. In this regard, swallow pattern analyzer data from a plurality of users can be uploaded to a server and used in the aggregate to refine swallow pattern recognition models, with the results being used to adapt the recognition models for download back to the individual users' smartphone devices.

Solid Vs. Liquid Detection

Some examples of solid and liquid swallowing data collected on different subjects are shown in FIG. 19. The rising edge in the graph corresponds to the inhalation and the falling edge corresponds to the exhalation. The arrows in the figure indicate when swallows happen.

FIG. 19 demonstrates the differences in derived signal between solid and liquid swallow. FIG. 19(*a*) shows the two cases of one subject, while FIG. 19(*b*) shows that of another subject. According to FIG. 19(*a*), it can be observed that the breaths are deeper during solid swallows and shallower during liquid swallows. While for FIG. 19(*b*), deeper breaths can be generally seen for liquid swallows, but breathing cycles for liquid can be very like the ones for solid swallows, such as the second swallow in the right graph in FIG. 19(*b*).

The scheme shown in FIG. 20 is proven to be effective to detect swallows from normal breathing cycles and differentiate solid and liquid swallows. In this scheme, the data received is first fed into a low pass filter in order to remover the steps caused by quantization and artifacts caused by motion. Peak-valley detection picks up the peaks fan valleys in order to separate and normalize different breathing cycles. Normalization is done because the lengths of breathing cycles are different among people and varies from time to time. The normalized breathing cycles are then fed into features extraction and feature selection modules, which would calculate features with discriminative power and select part of those for optimum performance. Comparing to the detection mechanism based on matched filter in our previous work, this machine learning based algorithm is able to provide better performance.

Support Vector Machine is used in the classification problem here because the decision boundary only depends on the support vectors whose number is usually small thus providing good generalizability, for which the SVM model is also simple and robust. We first use polykernel function to increase the dimensionality of features in case the classes are not linearly separable. Then the problem becomes finding the decision boundary $f(x)=w^T x+b$, such that the geometrical margin of the training set to the boundary is maximized. Geometrical margin is defined as $$\hat{\gamma} = \frac{y(w^T x + b)}{\|w\|},$$

function y calculates the function margin between the decision boundary and the training set, while $\|w\|$ normalizes the function margin into geometrical margin. Geometrical margin $\hat{\gamma}$ in this case reflects the confidence of classification. Therefore, by selecting the proper decision boundary $(w^T,b)$, the SVM model would be able to provide high classification confidence, which also means higher accuracy.

Table 5 shows the result of using machine learning algorithms in detecting solid and liquid swallows. In this result, machine learning algorithm is trained on 90% of data set from that of each subject, and tested on the remaining 10% of data set.

TABLE 5

Performance of solid/liquid swallow detection

| Subject | Solid/Liquid detection accuracy (%) |
|---|---|
| 1 | 94 |
| 2 | 100 |

TABLE 5-continued

Performance of solid/liquid swallow detection

| Subject | Solid/Liquid detection accuracy (%) |
|---|---|
| 3 | 90 |
| 4 | 74 |

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for monitoring food or beverage intake of a living subject, comprising:

a wearable breathing sensor adapted to be worn around the torso of the subject and being responsive of inhale-exhale movement of the subject's torso to produce a breathing signal expressed as electrical data, wherein the wearable breathing sensor includes (i) a chest-worn belt and (ii) at least one piezoelectric sensor placed between two elastic strips;

a classifier receptive of the electrical data and operative to classify the electrical data according to a predefined set of breathing patterns that include at least one apnea pattern indicating that the subject has swallowed during a breathing cycle;

a swallow pattern analyzer coupled to the classifier and operable to recognize food and beverage intake patterns in the electrical data, wherein the food and beverage intake patterns are associated with eating and drinking different types of food and beverage;

a processor programmed to store the classified electrical data in an associated data storage device;

a food intake analyzer that correlates a record of classified apnea patterns with food and beverage consumption logs entered by or on behalf of the subject; and a server configured to receive the correlation to enable remote monitoring of the living subject, wherein:

the classifier is configured to classify the electrical data according to a predefined set of breathing patterns that include:

a normal breathing pattern, a breathing cycle with exhale swallow pattern, and a breathing cycle with inhale swallow pattern, the classifier employs a plurality of matched filters that includes (i) a first matched filter for the normal breathing pattern, (ii) a second matched filter for the breathing cycle with exhale swallow pattern, and (iii) a third matched filter for the breathing cycle with inhale swallow pattern, the classifier is configured to use the plurality of matched filters to determine a plurality of similarity scores for the electrical data, each score of the plurality of similarity scores is associated with a pattern of the predefined set of breathing patterns, and the classifier is configured to classify the electrical data based on the plurality of similarity scores.

2. The system of claim 1 further comprising a signal shaping circuit that processes the breathing signal prior to submission to said classifier.

3. The system of claim 2 wherein said signal shaping circuit employs plural stages selected from the group consisting of impedance matching, drift control, DC damping, low pass filtering and amplification.

4. The system of claim 1 wherein said classifier is implemented by said processor programmed to analyze and classify the electrical data according to a predefined set of trained models stored in the associated data storage device.

5. The system of claim 4 wherein said processor is disposed within a portable electronic device.

6. The system of claim 4 wherein the wearable breathing sensor communicates wirelessly with said processor.

7. The system of claim 1 wherein the classifier is a support vector machine.

8. The system of claim 1 wherein the classifier is a support vector machine based on a polykernel function where the decision boundary is determined by maximizing the geometrical margin of training set data representing solid swallowing and liquid swallowing cases.

9. A method of monitoring food or beverage intake of a living subject, comprising:

placing a breathing sensor around the subject's torso to measure the subject's inhale-exhale movement and generating a breathing signal expressed as electrical data, wherein the breathing sensor includes (i) a chest-worn belt and (ii) at least one piezoelectric sensor placed between two elastic strips;

using electrical circuitry to automatically classify said electrical data according to a predefined set of breathing patterns that include at least one apnea pattern indicating that the subject has swallowed during a breathing cycle;

using the classified electrical data as a measure of the subject's food or beverage intake;

using a processor receptive of the classified electrical data to (i) store the classified electrical data in a data storage device associated with said processor and (ii) analyze the classified data to recognize food and beverage intake patterns associated with eating and drinking different types of food and beverage;

using the processor to correlate a record of classified apnea patterns with food and beverage consumption logs entered by or on behalf of the subject; and transmitting the correlation to a server to enable remote monitoring of the living subject, wherein:

the step of classifying said electrical data is performed by classifying the electrical data according to a predefined set of breathing patterns that include:

a normal breathing pattern, a breathing cycle with exhale swallow pattern, and a breathing cycle with inhale swallow pattern, the electrical circuitry employs a plurality of matched filters that includes (i) a first matched filter for the normal breathing pattern, (ii) a second matched filter for the breathing cycle with exhale swallow pattern, and (iii) a third matched filter for the breathing cycle with inhale swallow pattern, classifying said electrical data includes:

using the plurality of matched filters to determine a plurality of similarity scores for the electrical data, wherein each score of the plurality of similarity scores is associated with a pattern of the predefined set of breathing patterns, and the classifier is configured to classify the electrical data based on the plurality of similarity scores.

10. The method of claim 9 wherein the electrical circuitry used to automatically classify comprises a processor-implemented classifier utilizing at least one trained model.

11. The method of claim 9 further comprising performing signal shaping on said breathing signal prior to said classifying step.

12. The method of claim 9 wherein analyzing the classified electrical data is performed by comparing the classified electrical data to at least one trained model stored in the associated data storage device.

13. The method of claim 9 further comprising disposing the electrical circuitry to automatically classify said electrical data within the breathing sensor.

14. The method of claim 9 further comprising disposing the electrical circuitry to automatically classify said electrical data within a portable electronic device.

15. The method of claim 9 further comprising wirelessly communicating the electrical data from the breathing sensor to the electrical circuitry to automatically classify said electrical data.

16. The method of claim 9 wherein the electrical circuitry to automatically classify implements a support vector machine.

17. The method of claim 9 wherein the electrical circuitry to automatically classify implements a support vector machine based on a polykernel function where the decision boundary is determined by maximizing the geometrical margin of training set data representing solid swallowing and liquid swallowing cases.

* * * * *